US008094772B2

(12) United States Patent
Grass et al.

(10) Patent No.: US 8,094,772 B2
(45) Date of Patent: Jan. 10, 2012

(54) RECONSTRUCTION UNIT FOR RECONSTRUCTING A FINE REPRODUCTION OF AT LEAST A PART OF AN OBJECT

(75) Inventors: Michael Grass, Buchholz in der Nordheide (DE); Jens Berg, Hamburg (DE); Cristian Lorenz, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 625 days.

(21) Appl. No.: 12/158,069

(22) PCT Filed: Dec. 8, 2006

(86) PCT No.: PCT/IB2006/054702
§ 371 (c)(1),
(2), (4) Date: Jun. 19, 2008

(87) PCT Pub. No.: WO2007/072281
PCT Pub. Date: Jun. 28, 2007

(65) Prior Publication Data
US 2009/0003513 A1 Jan. 1, 2009

(30) Foreign Application Priority Data

Dec. 20, 2005 (EP) .................................... 05112496

(51) Int. Cl.
*A61B 6/03* (2006.01)
(52) U.S. Cl. ................. 378/8; 378/4; 382/131
(58) Field of Classification Search .................. 378/4, 8; 382/128–131; 345/424
See application file for complete search history.

(56) References Cited

U.S. PATENT DOCUMENTS

| 6,526,117 B1 | 2/2003 | Okerlund et al. |
| 6,628,743 B1 | 9/2003 | Drummond et al. |
| 2003/0016782 A1 | 1/2003 | Kaufman et al. |
| 2003/0016851 A1 | 1/2003 | Kaufman et al. |

FOREIGN PATENT DOCUMENTS

| WO | WO02103629 | * 12/2002 |
| WO | 2004057539 | 7/2004 |
| WO | 2004111936 A1 | 12/2004 |
| WO | 2005008597 A2 | 1/2005 |
| WO | 2005048193 A1 | 5/2005 |

OTHER PUBLICATIONS

Montagnat et al., Spatial and temporal shape constrained deformable surfaces for 3D and 4D medical image segmentation, 2000, INRIA research Report No. 4078, pp. 549-552.* Simon et al., Cardiac Motion Extraction Using 3D Surface Matching in Multislice Computed Tomography, Sep. 2004, MICCAI 2004, LNCS 3217, pp. 1057-1059.*
Manzke, R., et al.; Automatic phase determination for retrospectively gated cardiac CT; 2004; Med. Phys.; 31(12) 3345-3361.
Vembar, M., et al.; A dynamic approach to identifying desired physiological phases for cardiac imaging using multislice spiral CT; 2003; Med. Phys.; 30(7)1683-1693.

* cited by examiner

*Primary Examiner* — Edward Glick
*Assistant Examiner* — John Corbett (57) ABSTRACT

A reconstruction unit is provided for receiving a sequence of data sets, the data sets representing structural information of the object. The reconstruction unit performs receiving scheduling information related to the data sets of the sequence of data sets. Then reconstructing a sequence of coarse reconstructions of the object by using the sequence of data sets and the scheduling information. Afterwards a sequence of adapted models of the object is generated by adapting a respective model to each of the coarse reconstructions. Then a motion of a predetermined portion of each of the adapted models is determined and a specific data set of the sequence of data sets is selected, wherein the specific data set corresponds to the adapted model with the minimum motion of the predetermined portion. Finally the reconstruction unit performs reconstructing a fine reconstruction of at least the part of the object using the specific data set.

20 Claims, 5 Drawing Sheets

RECONSTRUCTION UNIT FOR RECONSTRUCTING A FINE REPRODUCTION OF AT LEAST A PART OF AN OBJECT

The invention relates to a reconstruction unit for reconstructing a fine reproduction of at least a part of an object, a corresponding method, an examination apparatus, a computer-readable medium and a program element. In particular, the invention relates to a reconstruction unit for reconstructing a fine reproduction of at least a part of an object, wherein the reproduction is executed on data detected by a tomography device.

Deploying computer tomography (CT) for object reconstruction aims to scan an object and to reconstruct a reproduction of the object, which object is enclosed by a body. The non-invasive method of scanning the object is a common procedure to obtain information about the object for diagnostic purposes.

Usually an image of the object is generated. The image can be analyzed and an abnormality of an inner structure of the object may be detected. CT scanning is quite often deployed to obtain information of a heart in the body of an human being e.g. calcification in the coronary arteries can be detected.

Since the heart is always in motion the reconstructed pictures may be blurry depending on the phase point of the cardiac cycle when the scan was performed or the projection data were selected and the image of the heart was reconstructed. The phase point determines the center of the interval of the cardiac cycle, or also named RR-interval, were the projection data have been selected or measured.

The automatic determination of an applicable phase point for retrospectively gated cardiac reconstruction remains as one of the key problems for CT based non-invasive coronary angiography. The determination of an applicable phase point can improve the quality of a reconstructed image of an object. For finding an applicable phase point as a first step, model based approaches have been used, followed by image processing based methods.

An image based approach is known from R. Manzke, et al.: Automatic phase determination for retrospectively gated cardiac CT, Medical Physics, Vol 31, No. 12, December 2004.

A model based approach is known from Vembar, et al.: A dynamic approach to identifying desired physiological phases for cardiac imaging using multislice spiral CT, Medical Physics, Vol. 30, No. 7, July 2003.

Further information can be found in U.S. Pat. No. 6,628,743 B1.

It may be desirable to provide efficient object reconstruction.

According to an exemplary embodiment of the present invention a reconstruction unit for reconstructing a fine reproduction of at least a part of an object is provided, wherein the reconstruction unit is adapted for receiving a sequence of data sets, the data sets representing structural information of the object. In parallel scheduling information related to the data sets of the sequence of data sets is received. Then a sequence of coarse reconstructions of the object is reconstructed by combining the sequence of data sets and the scheduling information. Afterwards a sequence of adapted models of the object is generated by adapting a respective model, in particular a basic model, to each of the coarse reconstructions. With the adapted models a motion of a predetermined portion of each of the adapted models is determined. Then a specific data set of the sequence of data sets is selected, wherein the specific data set corresponds to the adapted model with the minimum motion of the predetermined portion. Finally a fine reproduction of at least the part of interest of the object is reconstructed using the specific data set.

According to a further exemplary embodiment of the present invention, a method for reconstructing a fine reproduction of at least a part of an object is provided. The method comprises receiving a sequence of data sets, the data sets representing structural information of the object. The method also comprises receiving scheduling information related to the data sets of the sequence of data sets. Then reconstructing of a sequence of coarse reconstructions of the object is performed by using the sequence of data sets and the scheduling information. Afterwards a sequence of adapted models of the object is generated by adapting a respective model to each of the coarse reconstructions. Then a motion of a predetermined portion of each of the adapted models is determined and a specific data set of the sequence of data sets is selected, wherein the specific data set corresponds to the adapted model with the minimum motion of the predetermined portion. Finally the method comprises reconstructing a fine reconstruction of at least the part of the object using the specific data set.

According to a further exemplary embodiment an examination apparatus for reconstructing a fine reproduction of at least a part of an object is provided, the examination apparatus comprising the reconstruction unit as described above. The examination apparatus further comprises a detector unit and a time scheduling unit, wherein the detector unit is connected to the reconstruction unit. Furthermore, the time scheduling unit is connected to the reconstruction unit and the detector unit is adapted for providing the data set containing structural information about the object. The time scheduling unit is adapted for providing the scheduling information related to the data set.

According to another exemplary embodiment of the present invention, a computer-readable medium is provided, in which a computer program for reconstructing a fine reproduction of at least a part of an object is stored, which, when being executed by a processor, is adapted to carry out the above-mentioned method.

According to a further exemplary embodiment of the present invention, a program element for reconstructing a fine reproduction of at least a part of the object is provided, which, when being executed by a processor, is adapted to carry out the above-mentioned method.

In this context retrospective gating is used to express the process of scanning an object continuously and afterwards analyzing of the gathered information. While the scanning of the object is performed a sequence of data sets is generated. These data sets may represent a digitized information of a projection of the object. Structural information of the object, in particular structural information of an interior area of the object may be contained in the projection data set. After having collected the plurality of data sets, particular data sets can be selected to reconstruct a reproduction of the object.

In the following a basic idea of the invention is described in greater detail.

The reconstruction unit may be adapted for receiving a sequence of data sets, wherein the data sets represent structural information of the object. Further the reconstruction unit may receive scheduling information related to the data sets of the sequence of data sets. The scheduling information may be gathered in parallel to the process of gathering the data sets. Each data set may have a corresponding scheduling information and thus, an order of the data sets belonging to the sequence of data sets is provided. The scheduling information may be seen as a time scale to relate the data sets to the scheduling information. Thus, each data set may have a timing information or a time point information to determine the point in time when the data set was recorded.

By using the sequence of data sets and the scheduling information it may be possible to reconstruct a sequence of coarse reconstructions of the object. This combination may allow to reconstruct a movement or motion of the scanned object. Information about the motion may be available by comparing subsequent coarse reconstructions of the model. Using a coarse reconstruction may quickly provide results of calculations and automated operations like mathematical comparisons of the models and in particular of specific elements of the models may be possible.

A coarse reconstruction or a coarse reproduction may use less information than a fine reconstruction or a fine reproduction. Thus, a fine reproduction may show a more detailed information of the object.

It may also be possible to use all available information of the data sets and thus, instead of reconstructing a coarse reconstruction to reconstruct a fine reconstruction, already in this phase of the process. Thereby the performance of the process may be reduced, however smaller landmarks, i.e. portions, may be observed or detected and the phase of minimum motion of the small portions may be detected. The fine reproduction, which may be used instead of the coarse reproduction, may be an image of high resolution.

An example of a coarse reconstruction may be a two dimensional sectional view with a low resolution or a three dimensional picture with a low resolution. In a two dimensional view or picture pixels may be used to mark different sub-structures of the object. Therefore pixels may provide grey scale values or color values to mark different sub-structures. Accordingly a three dimensional picture may use voxels to distinguish between different substructures. A low resolution of a three dimensional picture may have a spatial resolution of e.g. $64^{\wedge}3$ ($=64^3$) voxels or $128^{\wedge}3$ ($=128^3$) voxels.

These pictures may be recorded at different points in time. Thus, the time resolution may be 20 to 50 three dimensional pictures in a defined time period wherein the time period may be substantially 1 second. The time period may also be expressed by a sampling rate, which is the inverse value of the duration of a period.

Since the coarse reconstructions may be computer generated pictures, it may be possible to detect different sub-structures in the coarse reconstructions by methods of automatic image processing. Therefore processing of the coarse reconstructions with the reconstruction unit may be possible. The reconstruction unit may deploy e.g. filter operations to select the boarders of different structures.

Thus, it may also be possible that the reconstruction unit is able to automatically distinguish and recognize different sub-structures in the coarse reconstruction of the object. In other words, parts of a representation of a real physical object, in particular interior structures of the physical object, may be converted into a machine-readable format.

Having a machine-readable format of the structural information of coarse reconstructions, the reconstruction unit may be able to automatically generate a sequence of adapted models of the object by adapting a respective basic model to each of the coarse reconstructions. In particular the reconstruction unit may be able to adapt the basic model to the detected sub-structures of the coarse reconstructions.

A model may be a mesh model. A mesh model may comprise a plurality of lines and edges to rebuild a structure of an object. For rebuilding the structure of the object of interest, the mesh model may use an a priori knowledge about the structure of the object of interest. In other words the basic structure of the object or the inner structure of the object may be known in advance and a basic mesh model using this knowledge may be provided. Then, for reconstructing the individual form of the object of interest, the basic model may have to be adapted to the recognized structures of the coarse reconstructions, which may be an image of the object of interest.

The edges and lines of the model may make such a model virtually deformable. The higher the number of edges the higher the granularity or resolution of the model. Since the mesh model may be deformable the model may be adapted to the detected structures or sub-structures of the coarse reconstructions of the physical object. For this adaptation landmarks are deployed, which may be specific points for finding related points of the coarse reconstructions. Such landmarks may be a known artery or a known ventricle in case of a heart.

After having adapted a single model to a sequence of coarse reconstructions or after having generated a sequence of adapted models a motion of a portion of the mesh model may be determined. The motion may be determined by tracking the position of a known specific point of the model in the sequence of adapted models. An example for a specific point may be an edge of the mesh model.

A motion vector field of the portion of interest may be generated in order to determine the strength of the motion of that portion. A motion vector field is a plurality of motion vectors. Each motion vector may correspond to the relevant portion of the object and may indicate the strength of the motion of the relevant portion.

The portion may be selected in advance since the portion of the model may correspond to a relevant portion or area in the physical object.

Using the determined information about the motion may allow selecting a specific data set of the sequence of data sets, wherein the specific data set may correspond to the adapted model with the minimum motion of the predetermined portion. The relevant data set may be determined by backward tracking from the adapted model to the relevant data set. The backward tracking may be possible, since the sequence of data sets is linked to the scheduling information.

When the relevant data set of minimum motion may be found it may be possible to reconstruct a fine reconstruction of at least the part of the object using the relevant data set. There may be additional information available in the data set for reconstructing a fine reproduction, since not all the information available in the data set may be used for the coarse reconstruction. Using the additional information from the relevant data set may achieve a high granularity of the reproduction, i.e. with this additional information it may be possible to reconstruct a picture with a high resolution.

In other words, using the method of retrospectively gated object reconstruction may produce a plurality of projections or scanner data sets. Scanning an oscillating object may produce artifacts or un-sharp reconstructed structures. If the object may oscillate irregularly the plurality of data sets may contain data sets corresponding to phases or phase points or points in time of high motion activity and data sets corresponding to phases or phase points or points in time of minimum motion activity.

Finding the data sets corresponding to phase points of minimum activity of a part of interest of the object may allow a sharp reproduction of the part of interest of the object. The sharpness may be increased by using data sets corresponding to phase points of minimum or nearly no motion of the part of interest of the object. The sharpness in addition may be increased by using all information available in a data set for reconstructing the object. This may lead to a sharp image of high resolution or a fine reproduction of high resolution.

Providing a high resolution may mean that an area is represented by a higher number of voxel or pixel. Thus, more details of the part of interest of the object may be visualized. Therefore structures, which usually cannot be seen in unsharp pictures may now be visible. Thus, fine structures of the object may also be seen. The fine structures may be seen even if the models have been adapted to other coarse shapes, which may be located nearby or underneath the fine structures.

In the following, further exemplary embodiments of the reconstruction unit will be described. These embodiments apply also for the method for reconstructing a fine reproduction of at least a part of an object, for the examination apparatus, for the computer-readable medium, and for the program element.

According to a further exemplary embodiment of the present invention, the reconstruction unit is adapted for reconstructing a cardiac structure.

A reconstruction unit, which is adapted for reconstructing a cardiac structure may allow to reconstruct a fine reproduction of the heart or parts of the heart. Since such a reproduction is not limited to the selected portion it may be possible that other structures are reconstructed. Therefore small coronaries may be visible on such reproductions.

The models of a heart may be permanently stored in a reconstruction unit, which is adapted for reconstructing a cardiac structure since the reconstruction unit may only be used for analyses concerning the heart and the reconstructing unit may be optimized for reconstructing cardiac structures.

According to another exemplary embodiment of the present invention, the respective model is at least one selected from the group consisting of a mesh and a cardiac model.

Using a specific mesh or cardiac model may allow recognition of the different sub structures or different compartments of the cardiac anatomy. Therefore the detection and reconstruction process may be accelerated.

According to a further exemplary embodiment of the present invention the above-mentioned respective model comprises adaptable shapes.

The more shapes are provided by the relevant model the better reconstruction may be performed. Using as much information of the model as possible may result in a better and sharper fine reproduction of the cardiac anatomy.

According to a further exemplary embodiment of the present invention the fine reproduction is at least one selected from the group of a fine mesh, fine sub mesh, a high resolution computer picture, a vector graphic, a high resolution 2D picture, a high resolution 3D picture, a coronal sectional view, and a sagittal sectional view of the part of the object.

The different reproductions may provide exemplary reproductions, which may be used in a computer system for representing a physical object. The different reproductions may be different representations of the same set of data. The different representations may be selectively switched on to provide different views of the part of interest of the object or cardiac structure to an user.

According to a further exemplary embodiment of the present invention, the reconstruction unit is adapted to process scheduling information, which is a sequence of points in time.

The points in time may correspond to specific events. The sequence of points in time may be an ordered list, listing sampling points. Having an ordered list of points in time, which may correspond to a relevant data set recorded in that special point in time may allow to relate a specific data set to a point in time, the data set corresponds to. This information of the relationship of the data set and the relevant point in time may be used when backtracking for finding the relevant data set for the fine reproduction.

According to a further exemplary embodiment of the present invention, the reconstruction unit is adapted to process scheduling information, which is a sequence of phase points.

A phase may be a regularly repeating interval, which is a part of the cardiac cycle. The cardiac cycle is a sequence of phase points and a sequence of phases. The phase points may allow to relate a data set to a defined point in time of the cardiac phase.

According to a further exemplary embodiment of the present invention, the phase points are phase points of a cardiac phase.

According to another exemplary embodiment of the present invention, the reconstruction unit is adapted to receive scheduling information from an ECG (electro cardiogram) recording. An ECG recording is a plot which represents the activity of an heart over the time. High activity may be represented by a high amplitude. Low activity may be represented by a low amplitude in the plot. Therefore defined phases of the cardiac cycle may be seen on the plot.

The ECG may be recorded in parallel to the sampling of the data sets. Since the time is recorded when the relevant data set is sampled, the data set can be related to a phase of the cardiac cycle. The link may be made by a common point in time of the sequence of data sets and the scheduling information.

According to a further exemplary embodiment the reconstruction unit is adapted to process a sequence of data, which is a sequence of CT projection data sets. Computer tomography (CT) is a process of using digital processing to generate a three-dimensional image of the internal structure of an object under investigation (object of interest) from a series of two-dimensional X-ray images taken around a single axis of rotation. The reconstruction of CT images can be done by applying appropriate algorithms.

For each point in time, when a X-ray image is recorded, a set of data is generated. The generated set of data may include information about a direction or angle in relation to the object and the corresponding attenuation of a X-ray through the body or object.

According to another exemplary embodiment the reconstruction unit is adapted for selecting the specific data set by generating a set of motion vectors belonging to the predetermined portion of the model, wherein the set of motion vectors is generated at each position of the adapted models. Once a set of motion vectors is generated the absolute length of the set of motion vectors of the predetermined portion of the adapted models is determined.

It may be possible to select from the sequence of adapted models at least one adapted model, which offers the minimum motion of the portion of interest. Since the adapted model is adapted to a coarse reconstruction of a data set, the relevant data set can be determined. This determination may be possible since the coarse reproduction may be related to a phase point of a cardiac cycle, and thus the relevant phase point of the cardiac cycle may be determined. This phase point may be the phase point used in retrospectively gated cardiac reconstruction to achieve a good diagnostic image quality.

In the following, a further exemplary embodiment of the method will be described. This embodiment applies also for the reconstruction unit for reconstructing a fine reproduction of at least a part of an object, for the examination apparatus, for the computer-readable medium, and for the program element.

According to another exemplary embodiment of the present invention, the method comprises selecting the part of the object as a structure nearby a coronary.

A coronary may be not directly detectable and visual in a coarse reproduction of the part of the object. The coronary therefore may also be no part of the model.

However, for visualizing the coronary or a plurality of coronaries or another fine structure, a part of the object that is known to be in the neighborhood or lying underneath the coronary or the fine structure may be selected to be sharply reproduced. Indirectly and automatically the coronary may be visible on the sharp reproduction of the object.

In the following, further exemplary embodiments of the examination apparatus will be described. These embodiments apply also for the reconstruction unit for reconstructing a fine reproduction of at least a part of an object, for the method, for the computer-readable medium, and for the program element.

Furthermore, according to another exemplary embodiment of the present invention, the examination apparatus may comprise a memory unit wherein the memory unit is adapted for storing the sequence of data sets and the scheduling information.

Storing the information may allow to collect the information about the object and to analyze the information after collecting the information. Thus, backtracking may be possible.

According to another exemplary embodiment of the present invention the examination apparatus comprises a graphical user-interface.

The graphical user-interface may be adapted to display information calculated by the examination apparatus. The fine reproduction may be a graphical representation of a list of graphical information. The graphical user interface may convert this graphical information into an image, viewable by an user. The graphical user interface may also provide the option to select between different views of the fine reproduction of the object.

The graphical user interface may also provide the possibility to send commands to the examination apparatus, in particular to control the reconstruction unit. The whole process of reconstructing a fine reproduction may be controllable through the graphical user interface.

According to another exemplary embodiment of the present invention, the examination apparatus is at least one selected of the group consisting of a material testing apparatus, a baggage inspection apparatus, a medical application apparatus, a computer tomography apparatus, a coherent scatter computed tomography apparatus, a positron emission computed tomography apparatus, a single photon emission computed tomography apparatus, ultra sound apparatus, electron beam tomography apparatus, magnetic resonance apparatus, and an interventional 3D rotational X-ray device.

By use of such an examination apparatus information may be provided about an inner structure of an object.

It may be seen as the gist of an exemplary embodiment of the present invention that automatically a phase point is determined, which phase point allows to reconstruct a high resolution reproduction to achieve a good diagnostic image quality. For achieving this high resolution reproduction, a model is adapted to coarse reconstructions so that a series of adapted models can be reconstructed. From this consecutive adapted models areas of minimum motion can be determined. To improve the quality of the high resolution reproduction preferably just a portion of the model is selected, leading to better results then just using global information of motion of the whole object.

Also if the reconstruction process uses a structure different from the structure of interest, the knowledge about the position of the structure of interest can be used to focus on a structure nearby the structure of interest. Since these different structures may have similar motion properties a point in time, which is good for reconstructing the nearby structure may also be good for reconstructing the structure of interest.

Thus, the structure of interest may be visible, even if this structure may not be part of a model used for reconstruction.

These and other aspects of the present invention will become apparent from and elucidated with reference to the embodiments described hereinafter.

Exemplary embodiments of the present invention will be described in the following, with reference to the following drawings.

The illustration in the drawings is schematically. In different drawings, similar or identical elements are provided with the same reference numerals.

Figure 1:
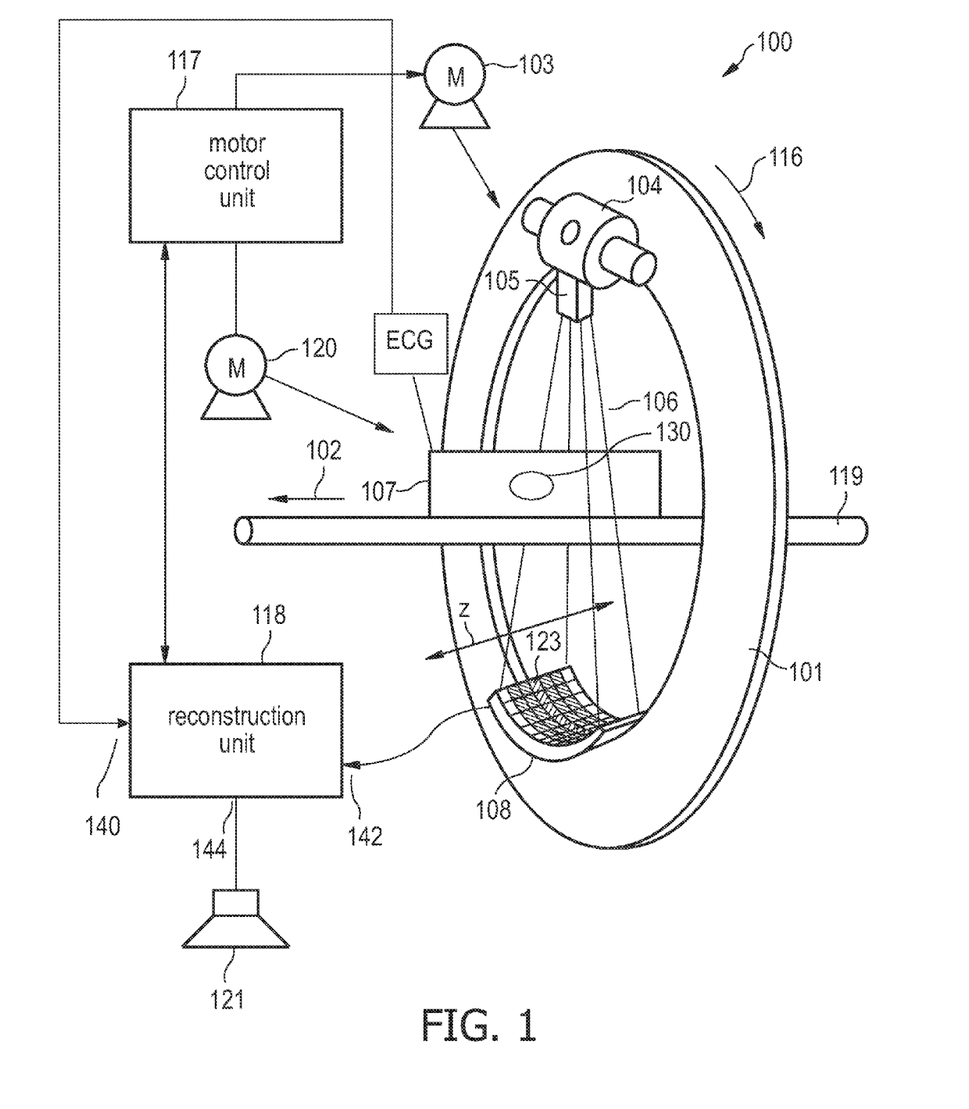
FIG. 1 shows a simplified schematic representation of an examination apparatus according to an exemplary embodiment of the present invention.

FIG. 1 shows an exemplary embodiment of a computed tomography scanner system according to the present invention.

The computer tomography apparatus 100 depicted in FIG. 1 is a cone-beam CT scanner. However, the invention may also be carried out with a fan-beam geometry. The CT scanner depicted in FIG. 1 comprises a gantry 101, which is rotatable around a rotational axis 102. The gantry 101 is driven by means of a motor 103. Reference numeral 104 designates a source of radiation such as an X-ray source, which, according to an aspect of the present invention, emits polychromatic or monochromatic radiation.

Reference numeral 105 designates an aperture system which forms the radiation beam emitted from the radiation source to a cone-shaped radiation beam 106. The cone-beam 106 is directed such that it penetrates an object of interest 107 arranged in the center of the gantry 101, i.e. in an examination region of the CT scanner, and impinges onto the detector 108. As may be taken from FIG. 1, the detector 108 is arranged on the gantry 101 opposite to the source of radiation 104, such that the surface of the detector 108 is covered by the cone beam 106. The detector 108 depicted in FIG. 1 comprises a plurality of detector elements 123 each capable of detecting X-rays which have been scattered by or passed through the object of interest 107.

The detector 108 may be a multi slice detector to increase the resolution in the z axis.

During scanning the object of interest 107, the source of radiation 104, the aperture system 105 and the detector 108 are rotated along the gantry 101 in the direction indicated by an arrow 116. For rotation of the gantry 101 with the source of radiation 104, the aperture system 105 and the detector 108, the motor 103 is connected to a motor control unit 117, which is connected to a control unit 118 (which might also be denoted as a calculation, determination unit or reconstruction unit).

In FIG. 1, the object of interest 107 is a human being which is disposed on an operation table 119. During the scan of a heart 130 of the human being 107, while the gantry 101 rotates around the human being 107, the operation table 119 displaces the human being 107 along a direction parallel to the rotational axis 102 of the gantry 101. By this, the heart 130 is scanned along a helical scan path. The operation table 119 may also be stopped during the scans to thereby measure signal slices. It should be noted that in all of the described cases it is also possible to perform a circular scan, where there is no displacement in a direction parallel to the rotational axis 102, but only the rotation of the gantry 101 around the rotational axis 102.

Moreover, an electrocardiogram (ECG) device 135 is provided which measures an electrocardiogram of the heart 130 of the human being 107 while X-rays attenuated by passing the heart 130 are detected by detector 108. The data sets detected by detector 108 are transmitted to the control unit 118 via interface or input terminal 142. The data related to the measured electrocardiogram are transmitted to the control unit 118 via interface or input terminal 140.

Further, it shall be emphasized that, as an alternative to the cone-beam configuration shown in FIG. 1, the invention can be realized by a fan-beam configuration. In order to generate a primary fan-beam, the aperture system 105 can be configured as a slit collimator.

The detector 108 is connected to the control unit 118. The control unit 118 receives the detection result in the form of a sequence of data sets, i.e. the read-outs from the detector elements 123 of the detector 108 and determines a scanning result on the basis of these read-outs. Furthermore, the control unit 118 communicates with the motor control unit 117 in order to coordinate the movement of the gantry 101 with motors 103 and 120 with the operation table 11.

The control unit 118 may be adapted for reconstructing an image from read-outs or data sets of the detector 108. A reconstructed image or fine reproduction generated by the control unit 118 may be output to a display or graphical user-interface 121.

The graphical user-interface 121 is connected to the interface or output terminal 144. The output 144 provides a bidirectional communication with the reconstruction unit 118. Therefore information can be displayed and control signals can be sent to the reconstruction unit.

Instead or in addition to the graphical user-interface 121 the reconstructed image, which may also be a digital image, is provided to a storage device (not shown in FIG. 1) or a data communication network. The data communication network may be an ATM (asynchronous transfer mode) or Ethernet based network and providing telemedicine applications.

The control unit 118 may be realized by a data processor to process read-outs from the detector elements 123 of the detector 108.

The computer tomography apparatus shown in FIG. 1 captures multi-cycle cardiac computer tomography data of the heart 130. In other words, when the gantry 101 rotates and when the operation table 119 is shifted linearly, then a helical scan is performed by the X-ray source 104 and the detector 108 with respect to the heart 130. During this helical scan, the heart 130 may beat a plurality of times. During these beats, a plurality of cardiac computer tomography data are acquired. Simultaneously, an electrocardiogram is measured by the electrocardiogram unit 135. After having acquired these data, the data are transferred to the control unit 118, and the measured data may be analyzed retrospectively.

The measured data, namely the cardiac computer tomography data and the electrocardiogram data are processed by the reconstruction unit 118 which may be further controlled via a graphical user-interface (GUI) 121. This retrospective analysis is based on a helical cardiac cone beam reconstruction scheme using retrospectively gating. It should be noted, however, that the present invention is not limited to this specific data acquisition and reconstruction.

The reconstruction unit 118 is adapted to analyze the multi-cycle cardiac computer tomography data detected by attenuating X-rays passing the heart 130 in the following manner, to automatically calculate phase points for spatially different cardiac structures using a model. A sequence of data sets is received from detector 108. The data sets represent structural information of the heart 130. In parallel scheduling information related to the data sets of the sequence of data sets is received by the reconstruction unit 118 from ECG 135. Then a sequence of coarse reconstructions of the heart 130 is reconstructed by using the sequence of data sets and the scheduling information.

A sequence of adapted models of the heart 130 is generated by adapting a respective model to each of the coarse reconstructions. Then a motion of a predetermined portion of each of the adapted models is determined and a specific data set of the sequence of data sets is selected. This specific data set corresponds to the adapted model with the minimum motion of the predetermined portion. Then a fine reproduction of at least the part of the object is reconstructed using the specific data set and the fine reproduction is displayed on the graphical user-interface 121 or sent to a remote graphical user-interface via a network.

In other words this means, that an automatic method is described to determine patient and anatomy selective optimal phase points in a fully automatic manner.

After the acquisition of the cardiac CT projection data set with parallel ECG 135 recording, a straightforward 4D reconstruction of the complete cardiac volume at low spatial resolution is performed. This data set may consist e.g. of 64^3 or 128^3 voxels and 20 to 50 different phases within the cardiac cycle. A 4D reconstruction is a reconstruction that combines a 3D image with the scheduling information as a fourth dimension.

Subsequently, a cardiac model consisting of adaptive shapes of the main compartments of the heart is fitted into one of the phases and propagated through the complete 4D data set. For all different phases the shape is adapted to the low resolution image data. Since the points used for the description of the model are assigned to the different compartments of the cardiac anatomy, their position can be tracked through the complete 4D data set.

As a measurement for the optimal phase point for the reconstruction of a certain cardiac structure, the absolute length of all motion vectors of all points belonging to this part of the model may be suitable. The minimum of this function than delivers the optimal phase point. Other measures are imaginable.

After having calculated the phase point for the cardiac structure of interest, this phase point is used in a high resolution reconstruction to achieve high diagnostic image quality.

The phase point may be good for structures like the coronaries, which may not directly be part of the model, to be determined by the phase point of their underlying structure or a structure nearby the coronaries.

Thus, phase points for different cardiac compartments for cardiac CT reconstruction can be determined. The detection can be performed for patient selective phase point for different coronary artery segments. Thus, patient individual characteristics of the cardiac phase can be regarded and a phase point can be derived in an anatomy selective manner. It is known from the statistical analysis of a large amount of cardiac image data sets that e.g. the right and the left coronary artery have their resting phase at different positions within the RR interval. The RR interval is the duration from the appearance of a R impulse in an ECG recording to the next R impulse. The R impulse shows in an ECG plot the start of a cardiac cycle. Usually 10-20% of the cardiac cycle after the appearance of the R impulse, the maximum motion of the heart may be expected, i.e. the phase of the compression of the left ventricle. In the close neighborhood of the R impulse less motion may be expected since the contraction of the atrium is finished.

Figure 2:
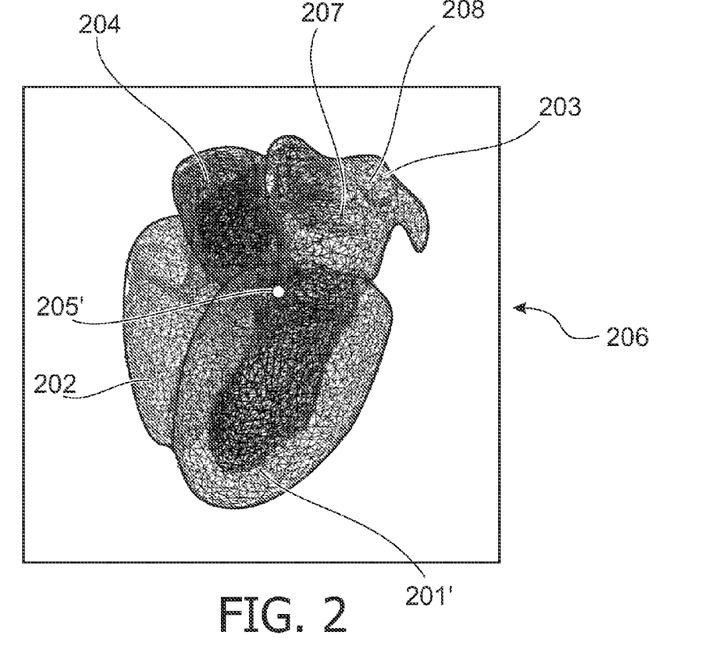
FIG. 2 shows a 3D model representation after adaptation to a low resolution 4D data set in an end systolic phase point.

FIG. 2 shows a 3D model representation after adaptation to a low resolution 4D data set in an end systolic phase point. In FIG. 2 different compartments 201', 202, 203 and 204 are shown in an end systolic phase point. The mesh model 206 comprises a plurality of edges 207 and lines 208 building triangular structures. The triangular structures represent the structure of the relevant compartment taken from a coarse reconstruction.

E.g. compartment 201' represents the left ventricle at the end systolic phase point.

A reference point 205' is shown in FIG. 2. Tracking the motion of the reference point 205' allows to determine the motion of a portion of the mesh model 206 the reference point 205' is belonging to.

Figure 3:
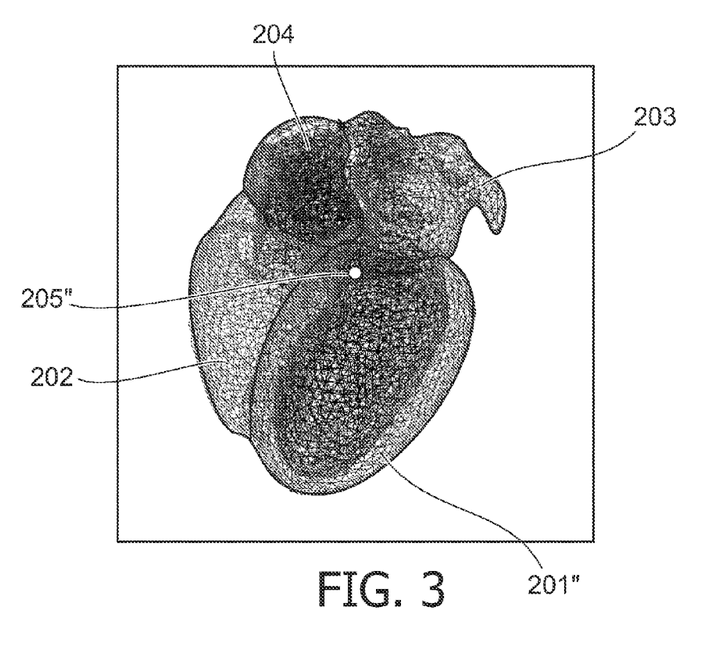
FIG. 3 shows a 3D model representation after adaptation to a low resolution 4D data set in an end diastolic phase point.

FIG. 3 shows a 3D model representation after adaptation to a low resolution 4D data set in an end diastolic phase point. In comparison with FIG. 2 it can be seen that the left ventricle 205" has a larger volume than the left ventricle 205' of FIG. 2. It can also be seen from FIG. 3 that reference point 205" has moved. Thus, by tracking the trajectory of reference point 205' and 205" and the calculation of the motion vectors in the relevant phases would indicate area of high motion. Therefore end systolic or end diastolic phase points may not applicable for a fine reproduction for the portion of the object 130 the reference point 205' is part of.

Figure 4:
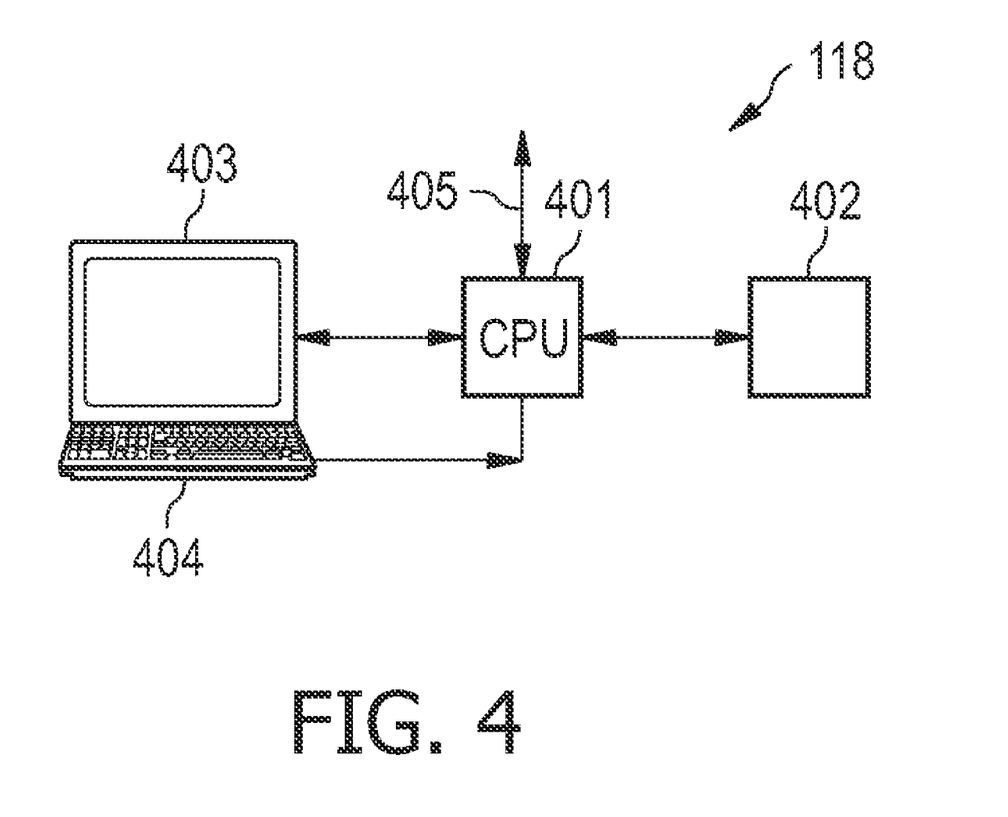
FIG. 4 shows an exemplary embodiment of an image processing device according to the present invention, for executing an exemplary embodiment of a method in accordance with the present invention.

FIG. 4 depicts an exemplary embodiment of a data processing device 118 or reconstruction unit according to the present invention for executing an exemplary embodiment of a method in accordance with the present invention. The data processing device 118 depicted in FIG. 4 comprises a central processing unit (CPU) or image processor 401 connected to a memory 402 for storing an image depicting an object of interest, such as a patient or an item of baggage. The data processor 401 may be connected to a plurality of input/output networks or diagnosis devices, such as a CT device. The data processor 401 may furthermore be connected to a display device 403, for example, a computer monitor or a graphical user-interface, for displaying information or an image computed or adapted in the data processor 401. An operator or user may interact with the data processor 401 via a keyboard 404 and/or other output devices, which are not depicted in FIG. 4.

Furthermore, via the bus system 405, it may also be possible to connect the image processing and control processor 401 to, for example, an ECG 135 and detector 108.

Figure 5:
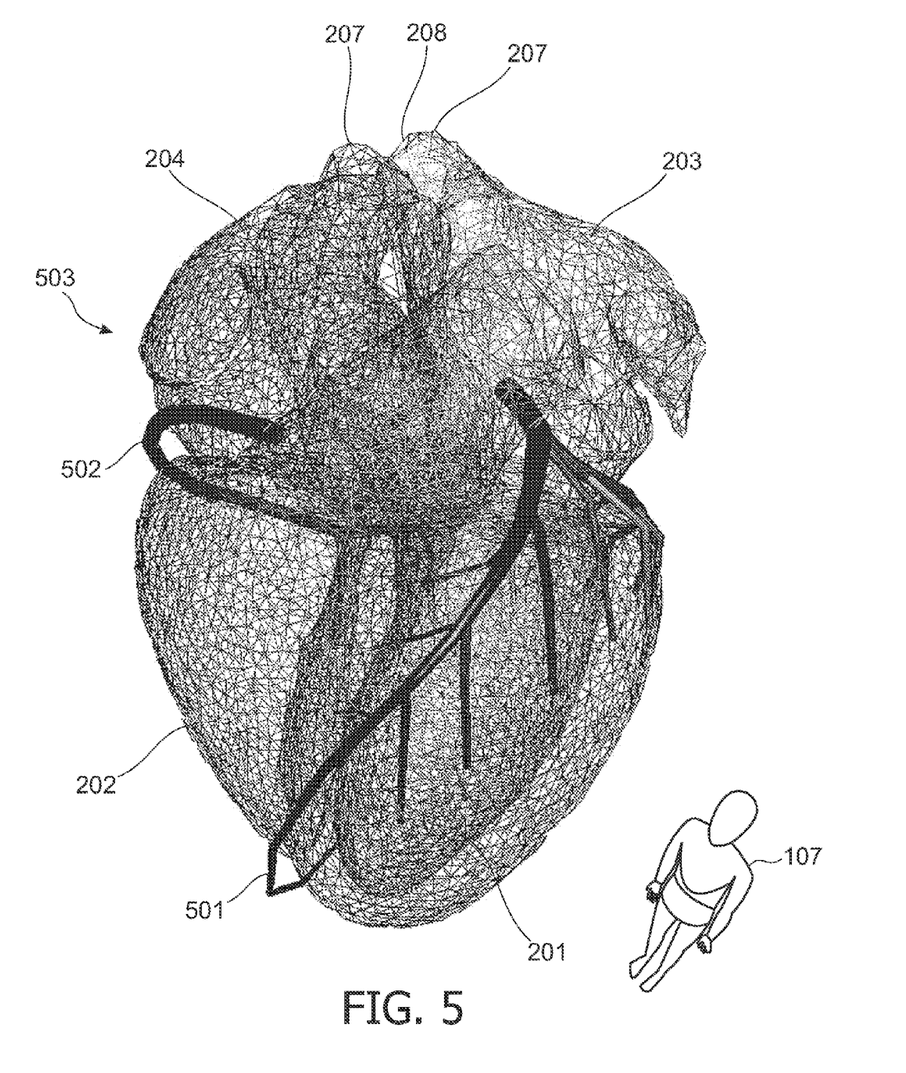
FIG. 5 shows a 3D mesh model with coronaries.

FIG. 5 shows a 3D mesh model with coronaries. The mesh model 503 is a model of the object of interest 130, e.g. the heart of a patient 107. The model of FIG. 5 is a basic model that is not adapted to patient individual anatomy.

The mesh model 503 has edges 207 and lines 208. By providing edges 207 and lines 208 the model has a computer readable and computer processable format, which may allow to adapt the model to an image of the heart by means of the computer. The compartments 201, 202, 203 and 204 are modeled and can be adapted to the relevant structures on a corresponding image. Additional the coronaries 501 and 502 are shown which lay in the neighborhood of the compartments 201 and 202. The left ventricle 201 is the underlying structure of coronary 501 which provides a plurality of branches. The compartment 202 is the underlying structure of coronary 502. The left ventricle 201 in FIG. 2 and FIG. 3 is labeled with 201' and 201" to show the different phases in which the left ventricle is depicted and to show the different sizes of the left ventricle in the different phases of the cardiac cycle.

The coronaries 501 and 502 may be not visible on a coarse reproduction. But determining a fine reproduction of the relevant compartments 201 and 202 can make the coronaries 501, 502 visible on the fine reproduction.

Figure 6:
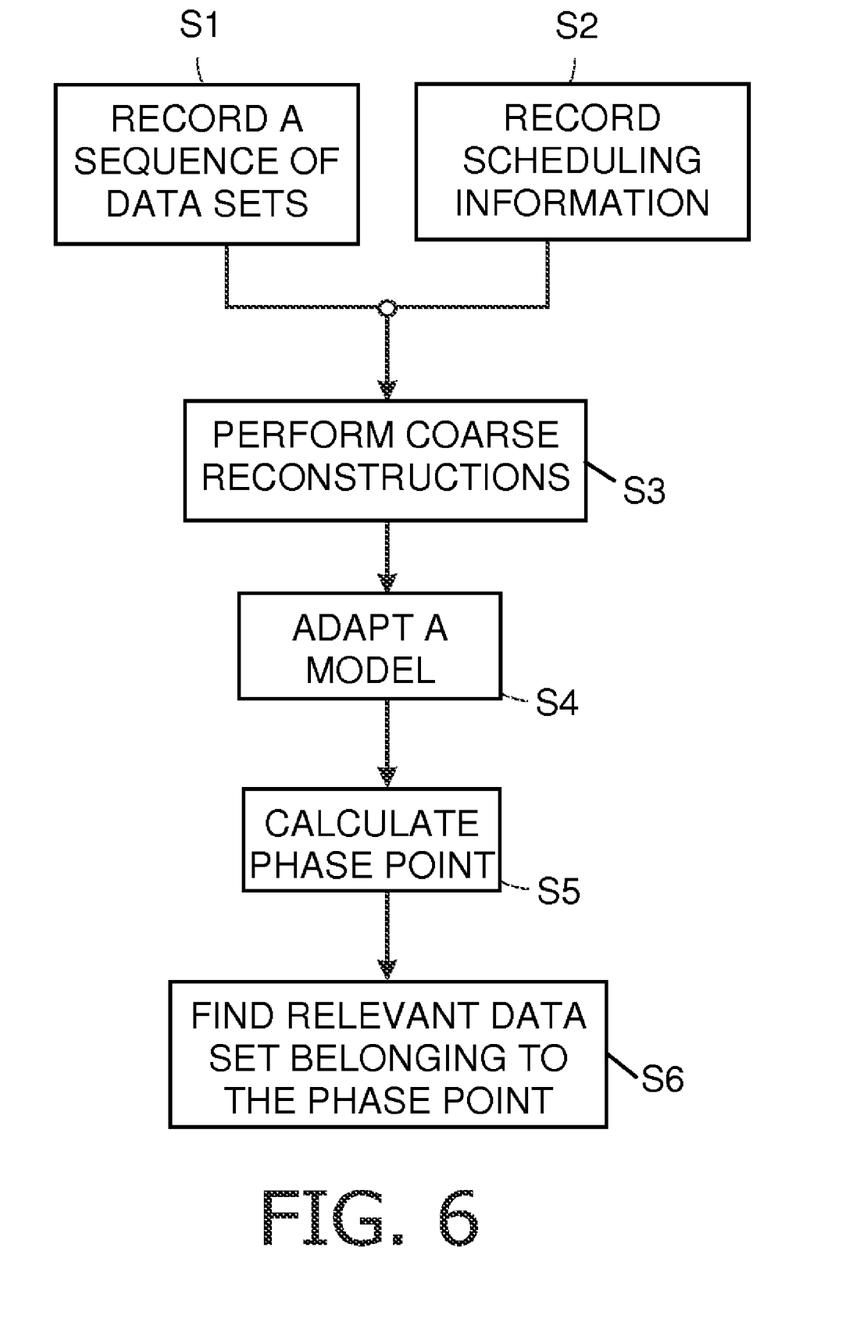
FIG. 6 shows a flow-chart of an exemplary method according to the present invention.

FIG. 6 shows a flow-chart of an exemplary method according to the present invention. The method starts with recording of a sequence of data sets in step S1 and with parallel recording of scheduling information in the form of ECG recording S2.

Then in step S3 a 4D coarse reconstructions of a sequence of cardiac volume is performed at low spatial resolution. For the reconstruction the data sets and the scheduling information of the ECG is combined.

After the reconstruction of the sequence of coarse reconstructions in step S4 a model is adapted to the coarse reconstructions and a sequence of adapted models is determined. Using these models allows to determine motion vectors.

In step S5 the minimum length of all motion vectors belonging to a part of the model is determined. With this information about the minimum motion an adequate phase point can be determined.

The phase point calculated in step S5 can be used in step S6 to find out the relevant data set belonging to the phase point. This data set is used to reconstruct a fine reconstruction.

Exemplary embodiments of the invention may be distributed as a software option to CT scanner console, imaging workstations or PACS workstations.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

The invention claimed is:

1. A reconstruction unit for reconstructing a fine reproduction of at least a part of an object, wherein the reconstruction unit is adapted for:

receiving a sequence of data sets, the data sets representing structural information of the object;

receiving scheduling information related to a sequencing of the sequence of data sets;

reconstructing a sequence of coarse reconstructions of the object by using the sequence of data sets and the scheduling information;

detecting sub-structures in the sequence of coarse reconstructions by processing the sequence of coarse reconstructions;

generating a sequencing of adapted models of the object by adapting a respective model to the detected sub-structures of each of the coarse reconstructions;

determining a motion of a predetermined portion, which is neighbored to the part of the object to be reconstructed, of each of the adapted models;

selecting a specific data set of the sequence of data sets, wherein the specific data set corresponds to the adapted model with the minimum motion of the predetermined portion; and reconstructing the fine reproduction of the at least the part of the object using the specific data set.

2. The reconstruction unit of claim 1, wherein the reconstruction unit is adapted for reconstructing a cardiac structure.

3. The reconstruction unit of claim 1, wherein the respective model is at least one selected from the group consisting of a mesh and a cardiac model.

4. The reconstruction unit of claim 1, wherein the respective model comprises adaptable shapes.

5. The reconstruction unit of claim 1, wherein the fine reproduction is at least one selected from the group of a fine mesh, fine sub mesh, a high resolution computer picture, a vector graphic, a high resolution 2D picture, a high resolution 3D picture, a coronal sectional view, and a sagittal sectional view of the part of the object.

6. The reconstruction unit of claim 1, wherein the reconstruction unit is adapted to process scheduling information which is a sequence of points in time.

7. The reconstruction unit of claim 6, wherein the reconstruction unit is adapted to process scheduling information which is a sequence of phase points.

8. The reconstruction unit of claim 7, wherein the phase points are phase points of a cardiac phase.

9. The reconstruction unit of claim 1, wherein the reconstruction unit is adapted for scheduling information from an ECG recording.

10. The reconstruction unit of claim 1, wherein the reconstruction unit is adapted to process a sequence of data sets, which is a sequence of CT projection data sets.

11. The reconstruction unit of claim 1, wherein the reconstruction unit is adapted for selecting the specific data set of the predetermined portion with minimum motion by:
generating a set of motion vectors belonging to the predetermined portion of the model, wherein the set of motion vectors is generated at each of the adapted models;
determining the minimum of the absolute length of the set of motion vectors of the predetermined portion of the adapted models.

12. An examination apparatus for reconstructing a fine reproduction of at least a part of an object, the examination apparatus comprising:
a reconstruction unit of claim 1;
a detector unit;
a time scheduling unit;
wherein the detector unit is connected to the reconstruction unit;
wherein the time scheduling unit is connected to the reconstruction unit;
wherein the detector unit is adapted for providing the data set containing structural information about the object;
wherein the time scheduling unit is adapted for providing the scheduling information related to the data set.

13. The examination apparatus of claim 12, further comprising:
a memory unit;
wherein the memory unit is adapted for storing the sequence of data sets and the scheduling information.

14. The examination apparatus of claim 12, further comprising:
a graphical user-interface;
wherein the graphical user interface is adapted for controlling the examination apparatus.

15. The examination apparatus of claim 12, wherein the examination apparatus is at least one selected of the group consisting of a material testing apparatus, a baggage inspection apparatus, a medical application apparatus, a computer tomography apparatus, a coherent scatter computed tomography apparatus, a positron emission computed tomography apparatus, a single photon emission computed tomography apparatus, ultra sound apparatus, election beam tomography apparatus, magnetic resonance apparatus, and an interventional 3D rotational X-ray device.

16. The reconstruction unit of claim 1, wherein the reconstruction unit is adapted for:
comparing each of the adapted models against one another to determine an adapted model with a minimum motion of the predetermine portion.

17. The reconstruction unit of claim 16, where selecting the specific data set of the sequence of data sets occurs by backward tracking from the adapted model with the minimum motion of the predetermine portion to the relevant data set.

18. A method for reconstructing a fine reproduction of at least a part of an object, the method comprising:
receiving a sequence of data sets, the data sets representing structural information of the object;
receiving scheduling information related to a sequencing of the sequence of data sets;
reconstructing a sequence of coarse reconstructions of the object by using the sequence of data sets and the scheduling information;
identifying structural information of the sequence of coarse reconstructions;
generating a sequence of adapted models of the object by adapting a respective model to each of the coarse reconstructions using the structural information of the sequence of coarse reconstructions;
determining a motion of a predetermined portion, which is neighbored to the part of the object to be reconstructed, of each of the adapted models;
selecting a specific data set of the sequence of data sets, wherein the specific data set corresponds to the adapted model with the minimum motion of the predetermined portion;
reconstructing a fine reproduction of at least the part of the object using the specific data set.

19. The method of claim 18, further comprising selecting the part of the object as a structure nearby a coronary.

20. A non transitory computer-readable medium, in which a computer program for reconstructing a fine reproduction of at least a part of an object is stored, which, when being executed by a processor, is adapted to carry out:
receiving a sequence of data sets, the data sets representing structural information of the object;
receiving scheduling information related to a sequencing of the sequence of data sets;
reconstructing a sequence of coarse reconstructions of the object by using the sequence of data sets and the scheduling information;
generating a sequence of adapted models of the object by adapting a respective model to each of the coarse reconstructions;
determining a motion of a predetermined portion, which is neighbored to the part of the object to be reconstructed, of each of the adapted models;
performing a comparison among the adapted models to determine an adapted model with a minimum motion of the predetermine portion;

selecting a specific data set of the sequence of data sets, wherein the specific data set corresponds to the adapted model with the minimum motion of the predetermined portion;

reconstructing a fine reproduction of at least the part of the object using the specific data set.

* * * * *